United States Patent [19]
Gottlieb et al.

[11] Patent Number: 6,007,560
[45] Date of Patent: Dec. 28, 1999

[54] BIOPSY FORCEPS HAVING DETACHABLE HANDLE AND DISTAL JAWS

[75] Inventors: Saul Gottlieb, Miami; Nigel MacDonald, Miami Shores; Matthew A. Palmer, Miami, all of Fla.

[73] Assignee: Symbiosis Corporation, Miami, Fla.

[21] Appl. No.: 08/931,753

[22] Filed: Sep. 16, 1997

Related U.S. Application Data

[63] Continuation of application No. 08/779,034, Jan. 6, 1997.
[51] Int. Cl.$^6$ .................................................... A61B 17/00
[52] U.S. Cl. ............................ 606/205; 606/174; 600/567
[58] Field of Search ................................... 600/564–568; 606/51, 52, 83, 174, 205–210

[56] References Cited

U.S. PATENT DOCUMENTS

| | | |
|---|---|---|
| 4,763,668 | 8/1988 | Macek et al. . |
| 4,944,741 | 7/1990 | Hasson . |
| 4,971,067 | 11/1990 | Bolduc et al. . |
| 5,304,024 | 4/1994 | Schuster . |
| 5,308,358 | 5/1994 | Bond et al. . |
| 5,368,606 | 11/1994 | Marlow et al. . |
| 5,385,561 | 1/1995 | Cerny . |
| 5,391,166 | 2/1995 | Eggers . |
| 5,454,378 | 10/1995 | Palmer et al. . |
| 5,507,297 | 4/1996 | Slater et al. . |
| 5,507,774 | 4/1996 | Holmes et al. . |
| 5,603,723 | 2/1997 | Aranyi . |
| 5,607,449 | 3/1997 | Tontarra . |
| 5,630,832 | 5/1997 | Giorano et al. . |

FOREIGN PATENT DOCUMENTS

| | | |
|---|---|---|
| 0 225 045 | 10/1987 | European Pat. Off. . |
| 0 529902 A2 | 3/1993 | European Pat. Off. . |
| 0 634139 A1 | 1/1995 | European Pat. Off. . |
| 3632786 A1 | 3/1988 | Germany . |
| 4332497 A1 | 3/1995 | Germany . |
| WO 94/22377 | 10/1994 | WIPO . |

Primary Examiner—Michael Buiz
Assistant Examiner—William W. Lewis
Attorney, Agent, or Firm—Finnegan, Henderson, Farabow, Garrett & Dunner, L.L.P.

[57] ABSTRACT

An endoscopic biopsy forceps instrument includes a distal jaws assembly detachable from a proximal handle assembly. The proximal handle assembly includes a centrally slotted shaft and a spool having a laterally seated cross block which passes through the central slot. The distal jaws assembly includes jaws mounted on a clevis at the distal end of a coil and coupled to a pull wire which extends through the coil to its proximal end. The proximal end of the coil is provided with a connecting sleeve provided with a frustoconical portion having double-helical threads for removably coupling the coil to a shaft having a distal frustoconical portion having double-helical threads. The proximal end of the pull wire is provided with a grooved mating member and the spool is provided with a locking assembly having a spring-biased push button latch for releasably engaging the grooved mating member. The grooved mating member has an elongate cylindrical distal portion, a central cylindrical portion having a relatively larger diameter, a proximal cylindrical grooved portion, and a proximal conical portion having a rounded apex. The elongate distal portion has a bore into which the pull wire is secured. The mating member end of the pull wire can be snapped into the locking assembly and the coil can be quickly and securely coupled to the shaft.

30 Claims, 8 Drawing Sheets

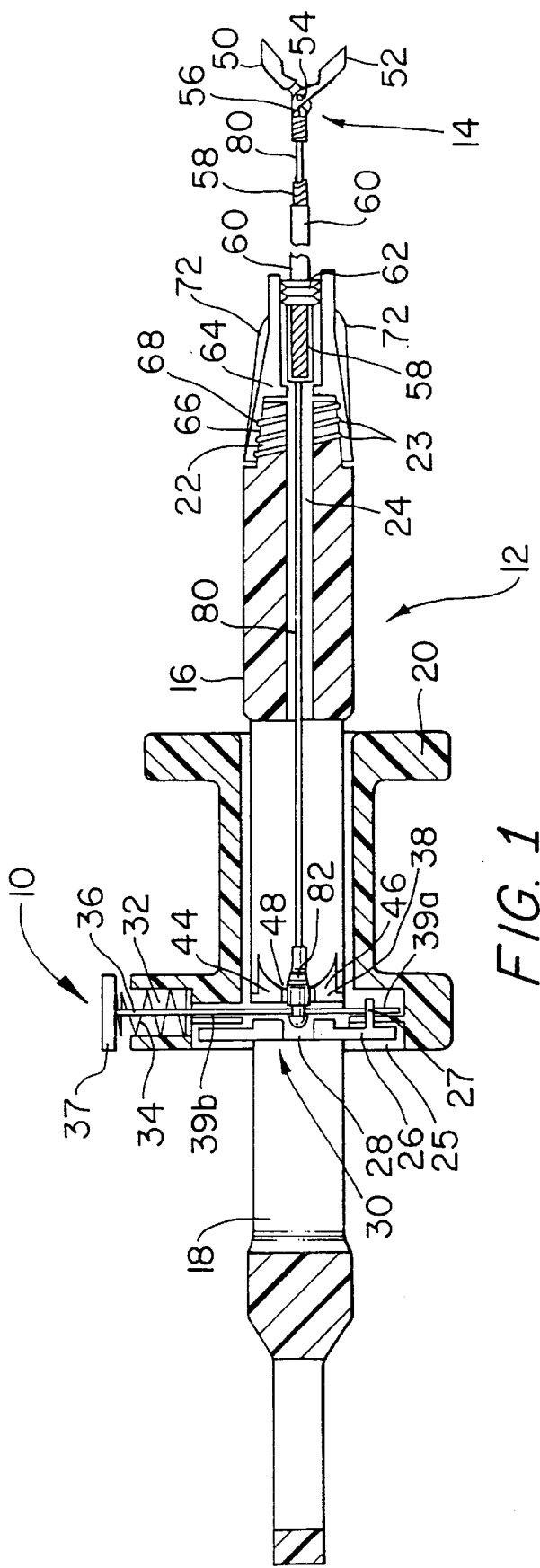
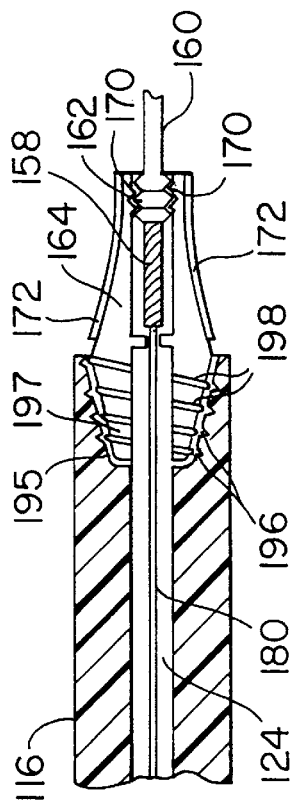
FIG. 1
FIG. 14

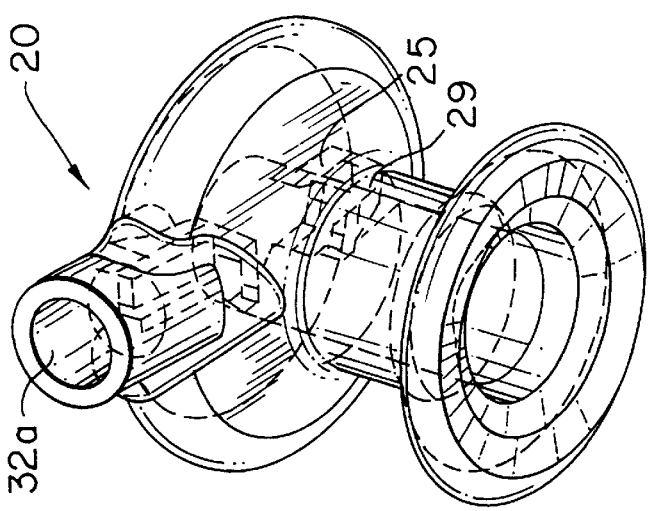
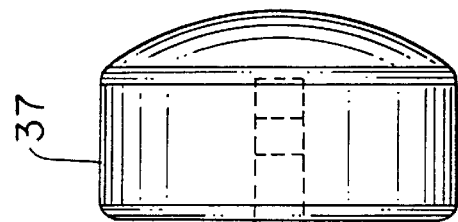
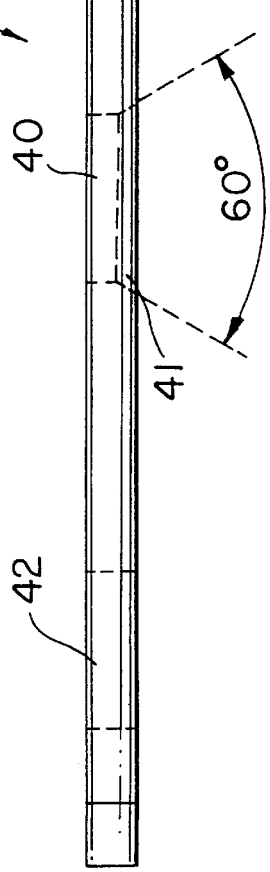
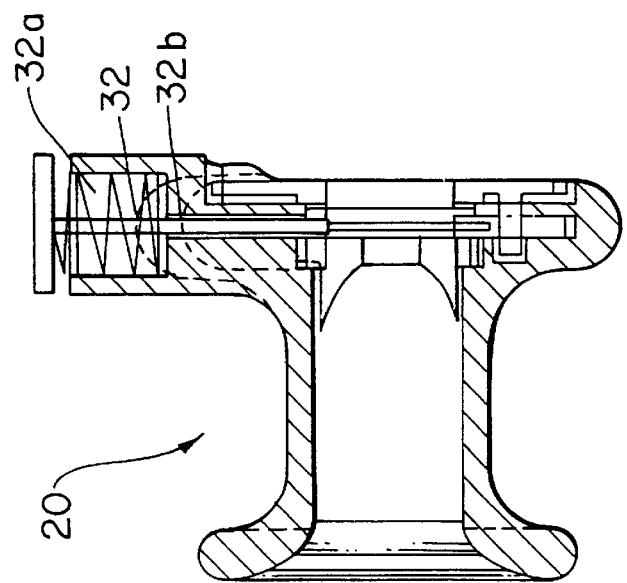

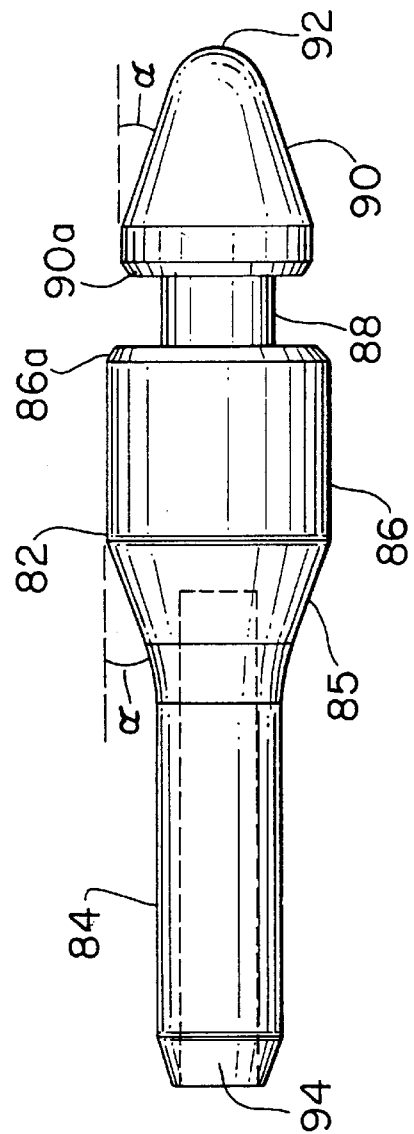
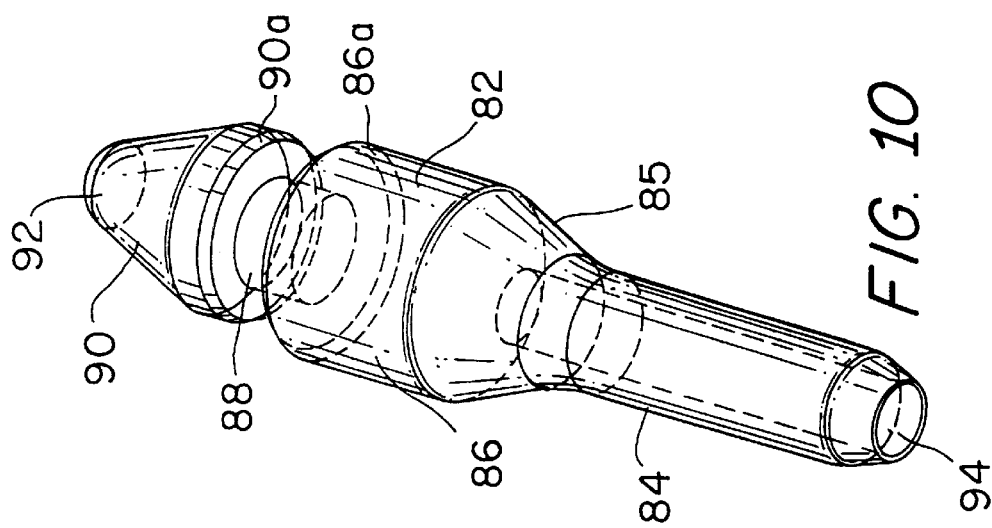

BIOPSY FORCEPS HAVING DETACHABLE HANDLE AND DISTAL JAWS

This is a continuation of application Ser. No. 08/779,034, filed Jan. 6, 1997.

This invention is related to co-owned U.S. Pat. No. 5,454,378, entitled "Biopsy Forceps Having a Detachable Proximal Handle and Distal Jaws", which is hereby incorporated by reference in its entirety herein.

BACKGROUND OF THE INVENTION

1. Field of the Invention

This invention relates broadly to surgical instruments. More particularly, this invention relates to endoscopic surgical instruments having detachable proximal handles.

2. State of the Art

Endoscopic surgery is widely practiced throughout the world today and its acceptance is growing rapidly. In general, endoscopic surgery involves the use of a camera or magnifying lens inserted through a tube, while a cutter, dissector, or other surgical instrument is inserted through another tube for purposes of manipulating and/or cutting an internal organ or tissue under view of the surgeon. In endoscopic biopsy procedures, typically, the camera is located in one lumen of a flexible endoscope while the biopsy cutter is placed through another lumen thereof.

Most endoscopic instruments have similar configurations with a proximal handle, an actuation mechanism, and distal end effectors coupled by a flexible tube or coil through which the actuation mechanism extends. The end effectors take many forms such as grippers, cutters, forceps, dissectors and the like.

Initially, endoscopic surgical instruments were very expensive, partly because they must be very small but still durable and reliable and the materials and manufacturing methods necessary to provide these features are expensive. Recently, however, a number of "disposable" endoscopic instruments have been introduced and their use is now widely accepted. One of the advantages of disposable endoscopic instruments over reusable instruments is that because they are used only a single time, there are no sterilization problems, (i.e., no risk of cross-contamination between patients) and no concerns about the dulling or nicking of blades or wearing of parts. However, in order to justify disposing of instruments after a single use, the instruments have to be much less expensive than the reusable tools. In order to manufacture the instruments less expensively, the disposable instruments therefore use less expensive materials. As a result, the disposable instruments potentially are less durable than the reusable instruments. It is recognized, however, that the less durable components of the disposable instruments are most often parts of the distal end effectors and that the proximal handle portion of a disposable instrument is substantially as durable as the proximal handle portion of a reusable instrument. Moreover, the distal end effectors are not so fragile that they can only withstand a single use. Despite manufacturer's recommendations to the contrary, some surgeons will sterilize disposable instruments and reuse them a few times in order to reduce "per procedure costs". Ultimately, however, it is the distal portion of the instrument which wears or breaks and mandates disposal of the entire disposable instrument.

Among the disposable endoscopic instruments in use today are a number of different types of biopsy forceps devices. These devices most often include very sharp opposing jaws for grasping and tearing tissue for biopsy. The jaws are mated with one another about a clevis pin which is mounted in a clevis. The clevis extends into a housing which is crimped to the distal end of a relatively long flexible coil. The proximal end of the coil is coupled to a handle having means for articulating the jaws. The handle generally includes a central slotted shaft about which a spool is disposed. A pull wire from the jaws extends through the coil and is attached to the spool while the coil is attached to the central shaft of the handle. Movement of the spool relative to the central shaft moves the pull wire relative to the coil and thus articulates the jaws at the distal end of the coil. In use, the jaws and coil are inserted through a flexible endoscope which is already in place in the patient's body. The surgeon guides the coil and jaws to the biopsy site while a nurse holds the handle. When the surgeon has located the jaws at the appropriate place, the nurse is instructed to operate the handle to articulate the jaws and grasp a biopsy sample. At the conclusion of the biopsy procedure, the entire forceps apparatus is either disposed of or cleaned and sterilized for re-use.

The known endoscopic biopsy forceps devices of the art have the drawback that the jaws wear out long before the useful life of the handle has expired. Thus, the entire instrument must be discarded when it is only a small portion of the instrument which is inoperative.

An endoscopic biopsy forceps device with detachable proximal handle and distal portions is known and described in U.S. Pat. No. 4,763,668 to Macek et al. It is a disadvantage of the Macek et al. detachable biopsy forceps device that attachment and detachment of the proximal and distal portions requires the screwing in and out of screws and an awkward rotation of a sleeve which makes the attachment and detachment procedures cumbersome.

Co-owned U.S. Pat. No. 5,507,297 to Slater et al. discloses laparoscopic instruments having detachable proximal handle and distal portions. These instruments have a distal assembly insertable and removable from a proximal handle assembly in one step actions. The distal assembly includes a tube, end effectors coupled to the tube, and a push rod coupled to the end effectors and slidable through the tube. The proximal handle assembly includes a tube sleeve for receiving the tube, manually operable actuating means, and a latch for coupling the push rod to the actuating means. The tube sleeve is provided with a ball or blade lock for holding the tube securely in place and the tube is provided with a circumferential groove for engaging the ball or blade lock. The latch is spring loaded, hinged, and has an inclined surface for quick coupling with the push rod and an unlatching surface which when biased by an unlatching member uncouples the push rod. The push rod is provided with a mating tip which engages the latch so that the manually operable actuating means causes reciprocal movement of the push rod within the tube to operate the end effectors. Coupling and uncoupling the proximal and distal assemblies is quick, one step, and substantially automatic. However, the coupling of the tube to the lock is complicated and expensive to manufacture.

Co-owned U.S. Pat. No. 5,454,378 to Palmer et al. discloses endoscopic instruments also having one step coupling and uncoupling. The handle assembly of the instrument includes coupling devices for removably coupling the handle to a coil and to pull wires. The proximal end of the coil is provided with a mating sleeve having a circumferential groove, and the proximal ends of the pull wires are provided with a mating tip assembly. The handle assembly includes a central slotted shaft carrying a spool having a cross block which passes through the central slot of the shaft. The distal end of the shaft is provided with a spring biased latch for engaging the circumferential groove of the mating sleeve of the coil. The cross block of the spool is provided with a pair of spring biased sliders for engaging the mating tip assembly of the pull wires. The mating sleeve has a tapered proximal end so that when it is inserted into the distal end of the handle shaft, the biased latch is moved open until the sleeve is inserted to the point where the circumferential groove is engaged by the latch. The cross block is provided with an internally tapered guide and the mating tip assembly of the pull wires is tapered to be received and guided by the guide. The sliders have angled faces for receiving the mating tip and locking around it. The coil and pull wires are thus coupled to the handle in a single motion by inserting the proximal end of the coil and pull wires into the distal end of the handle shaft. The mating sleeve and mating tip assembly automatically engage the latch and the sliders respectively and "snap" into place. During disengagement, the latch is operated by a push button at the distal end of the handle shaft. By pushing the push button, the latch releases the coil and the circumferential groove of the mating sleeve can be slid out of engagement with the latch by pulling the coil. Pulling the coil from the handle also pulls the pull wires which are coupled to the cross block containing the sliders, which in turn results in a pulling of the cross block of the spool. As the cross block moves proximally along the slotted shaft, a collar is engaged by a mechanism attached to the proximal end of the slotted shaft. The collar in turn engages angled extensions of the sliders, and forces the sliders apart, thereby releasing the mating tip assembly of the pull wires, and thus the handle from the distal assembly. While the instrument has proven effective in providing an endoscopic instrument having a handle separable from the distal assembly, the spool and shaft couplings each have a large number of parts and are expensive and complicated to manufacture. In addition, re-assembly of distal assembly into the handle requires precision alignment of the coil and pull wires relative to the spool and shaft couplings, which is time consuming.

In Europe, an endoscopic biopsy device having a detachable handle assembly is currently being marketed by Karl Schad. The device has a relatively simpler construction. The handle assembly includes a central slotted shaft carrying a spool having a cross block which passes through the central slot of the shaft and coupling devices for removably coupling the handle assembly to a coil and to a pull wire. The proximal end of the coil is provided with a substantially cylindrical connecting sleeve having internal threads and the distal end of the shaft is provided with external threads such that the connecting sleeve and the shaft are coupled together at their respective threads. The proximal end of the pull wire is provided with a mating tip assembly. The spool is provided with a spring biased latch which engages the mating tip assembly. The mating tip assembly is engaged by depressing the latch, inserting the mating tip assembly into a hole provided in the latch, and releasing the latch. While the Karl Schad device presents a viable method of constructing an endoscopic instrument having detachable handle and distal assemblies, the device is not ideal. In order to couple the handle assembly to the pull wire and to the coil, a cumbersome two step operation is required. First, the spring biased latch must be depressed in order to receive the mating tip assembly and released to engage the mating tip assembly. This is an inconvenient manner of coupling the pull wire to the spool. Next, the connecting sleeve must be inserted over the shaft and rotated many times relative to the shaft so that a secure threaded coupling is accomplished between the connecting sleeve and the shaft. This coupling method is time consuming.

SUMMARY OF THE INVENTION

It is therefore an object of the invention to provide an endoscopic biopsy forceps device where the proximal handle and the distal jaws are easily separable from each other so that the jaws may be discarded without disposing of the handle.

It is also an object of the invention to provide an endoscopic biopsy forceps device where the proximal handle and the distal jaws are easily attachable to each other so that the handle may be re-used with a new set of jaws.

It is another object of the invention to provide an endoscopic biopsy forceps device where the proximal handle and the distal jaws of the device are quickly attachable.

It is a further object of the invention to provide an endoscopic biopsy forceps device where the proximal handle and the distal jaws of the device are easily alignable for attachment.

It is also an object of the invention to provide an endoscopic biopsy forceps device which has a detachable proximal handle and distal jaws which is inexpensive and easy to manufacture.

In accord with the se objects which will be discussed in detail below, the biopsy forces of the present invention includes a proximal handle assembly and a distal jaws assembly. The proximal handle assembly includes a centrally slotted shaft provided with a distal portion having double-helical threads, and a spool having a laterally seated cross block which passes through the central slot. The spool is provided with a locking assembly having a spring-biased push button latch. The distal jaws assembly has a pair of jaws mounted on a clevis at the distal end of a coil and coupled to a pull wire which extends through the coil to its proximal end. The proximal end of the coil is provided with a sleeve having double-helical threads. The proximal end of the pull wire is provided with a grooved mating member which has an elongate cylindrical distal portion coupled to the pull wire, a frustoconical portion, a cylindrical central portion having a relatively larger diameter, a cylindrical proximal grooved portion, and a conical proximal portion having a rounded apex.

In assembling the biopsy forceps of the invention, the mating member on the pull wire is inserted into the locking assembly, such that the spring-biased push button latch automatically engages the grooved portion of the mating member thereby coupling the pull wire to the spool. The threaded connecting sleeve on the coil is then coupled to the distal portion of the shaft by engaging the two and turning the sleeve one half turn. The proximal handle and distal jaw assemblies are detached from one another by unthreading the threaded connecting sleeve from the shaft and depressing the push button spring-biased latch.

Preferred aspects of the invention include providing internal double helical threads on the connecting sleeve and external threads double helical threads at the shaft tip. In addition the threaded portion at the shaft tip is frustoconical in shape and the internally threaded portion of the sleeve has a frustoconical opening for receiving the shaft tip.

Additional objects and advantages of the invention will become apparent to those skilled in the art upon reference to the detailed description taken in conjunction with the provided figures.

BRIEF DESCRIPTION OF THE DRAWINGS

FIG. 1 is a broken side elevation view in partial section of a biopsy forceps instrument according to the invention;

FIG. 3 is side elevation in partial view of a spool of the biopsy forceps instrument of FIGS. 1 and 2;

FIG. 4 is a transparent perspective view of the spool of FIG. 3;

FIG. 5 is an enlarged side elevation view of a push button latch of the biopsy forceps instrument of FIGS. 1 and 2;

FIG. 9 is an enlarged side elevation view of the grooved mating member of the biopsy forceps instrument of the invention;

FIG. 10 is a transparent perspective view of the grooved mating member of FIG. 6;

FIG. 14 is a broken side elevation view in partial section of a second embodiment of the coil to the shaft mating portion of the biopsy forceps instrument of the invention.

DETAILED DESCRIPTION OF THE PREFERRED EMBODIMENTS

Figure 2:
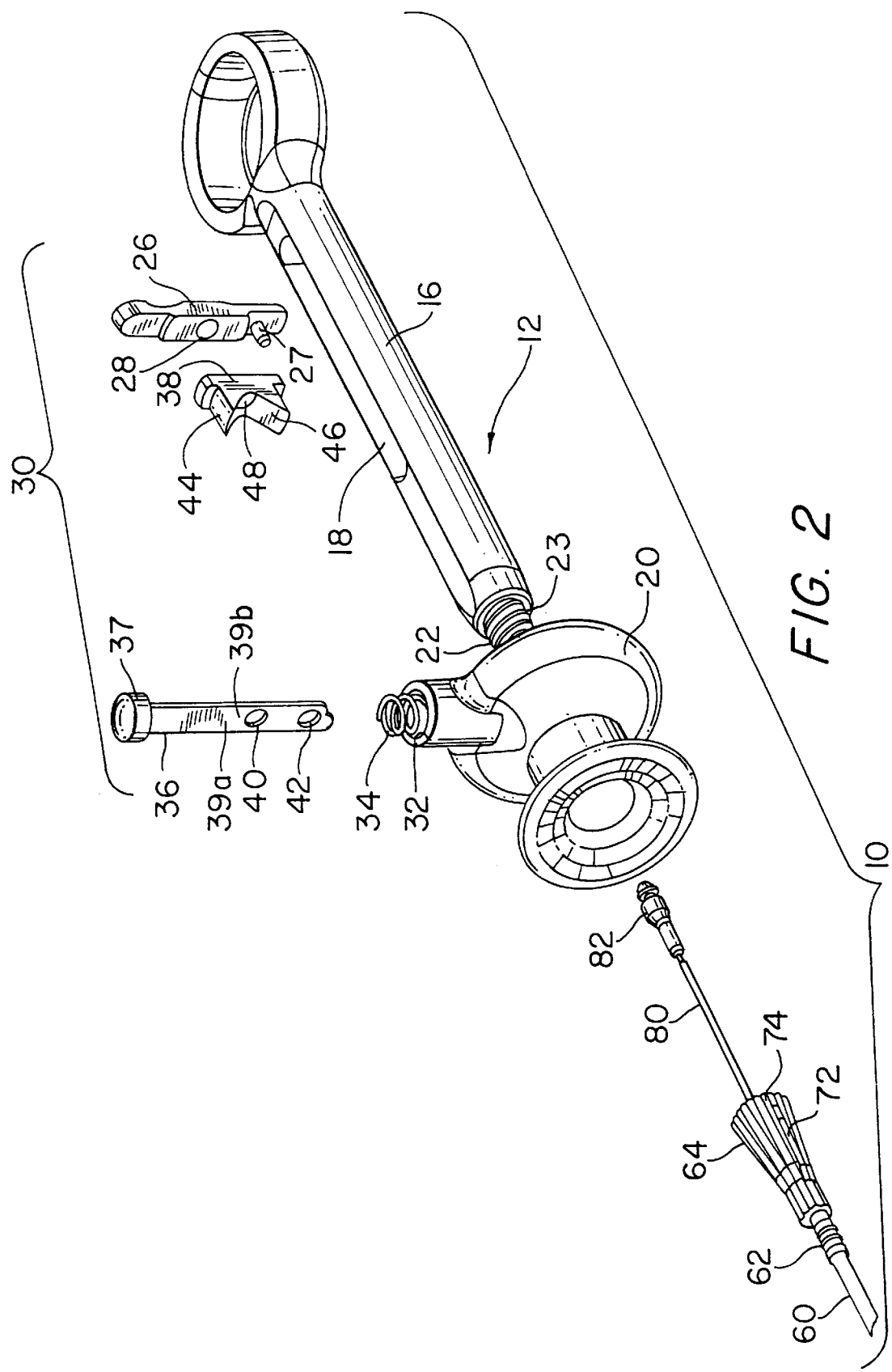
FIG. 2 is a broken exploded perspective view of the proximal portion of the biopsy forceps instrument of FIG. 1.
Figure 6:
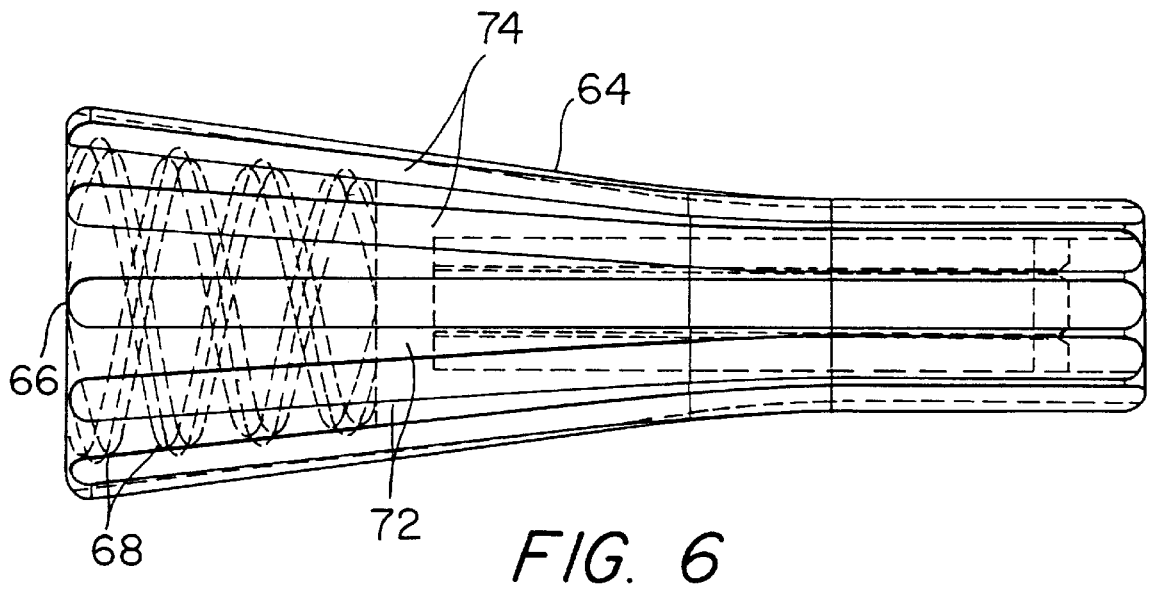
FIG. 6 is an enlarged transparent side elevation view of a threaded connecting sleeve of the biopsy forceps instrument of FIGS. 1 and 2.
Figure 7:
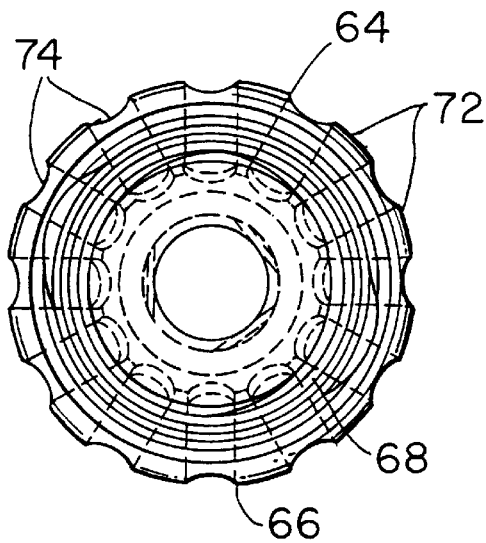
FIG. 7 is a proximal end view of the threaded connecting sleeve of FIG. 3.
Figure 8:
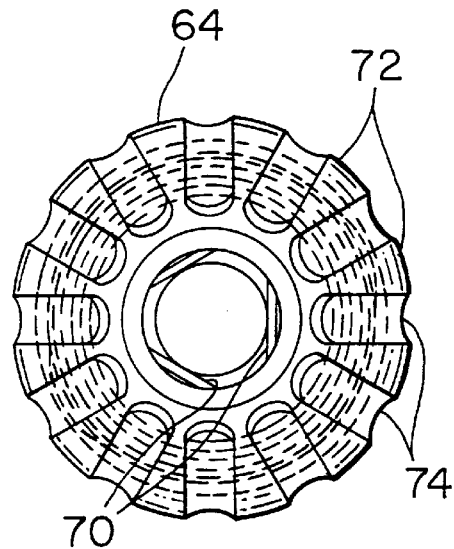
FIG. 8 is a distal end view of the threaded connecting sleeve of FIG. 3.

Turning now to FIGS. 1 through 4, a biopsy forceps instrument 10 according to the invention generally includes a proximal handle assembly 12 and a distal jaw assembly 14. The proximal handle assembly 12 includes a shaft 16 having a central slot 18 and a spool 20 slidable on the shaft 16. The distal end of the shaft 16 is provided with a frustoconical shaft tip 22 having external double-helical threads 23 and a throughbore 24. The spool 20 is provided with a cross block 26 having a distal nub 27 and a central hole 28. The cross block 26 is seated in a channel 25 in the proximal portion of the spool 20 and passes through the central slot 18 of the shaft 16. The nub 27 of the cross block 26 locks into a hole 29 in the floor of the channel 25 and extends into a latch receptacle, described below. The central hole 28 is sized to permit the proximal end of a mating member, described below, to enter therein.

Referring to FIGS. 1 through 5, the proximal end of the spool 20 is provided with a locking assembly 30 having a radially extending latch receptacle 32, a spring 34, and a push button latch 36. As seen best in FIG. 3, the latch receptacle 32 includes a cylindrical portion 32a and a channel portion 32b. The spring 34 is seated in the cylindrical portion 32a of the latch receptacle 32 and the latch 36 extends through the spring and into the channel portion 32b. A seen best in FIG. 4, the latch 36 includes a head 37, a distal side 39a, a proximal side 39b, a catch hole 40, and an interlock hole 42. The catch hole 40 is large enough to receive a mating member located on the pull wire, as described below, and preferably is provided with an approximately 60° chamfer around the catch hole 40 on the distal side 39a. The chamfer 41 facilitates movement of the mating member through the catch hole. The nub 27 on the cross block 26 extends through the interlock hole 42. The interlock hole 42 is larger than the nub 27, thereby permitting the latch 36 to move within the receptacle 32 relative to the nub 27. In addition, extension of the nub 27 through the interlock hole 42 prevents the latch 36 from being released from the receptacle 32. The spring 34 abuts the head 37 of the latch and biases the latch 36 in the receptacle 32 such that the catch hole 40 is in a partially overlapping alignment with a guide hole, as described below.

Turning back to FIGS. 1, 2, and 3, the spool 20 is also provided with a guide 38 which has laterally and distally extending portions 44, 46 which taper to a guide hole 48. The guide 38 is located in the spool 20 distal of the latch 36 and guides a mating member on the pull wire into engagement with the latch 36 as described hereinafter.

As seen in FIG. 1, the distal jaw assembly 14 includes a pair of sharp opposing jaws 50, 52 for grasping and tearing tissue for a biopsy sample. The jaws 50, 52 are preferably arranged about a clevis pin 54 which is mounted in a clevis 56 at the distal end of a relatively long flexible coil 58. The coil 58 is preferably covered in a substantially smooth wrap 60 which preferably has at its proximal end a plurality of barbs 62. As seen in FIGS. 1 and 2 and 6 through 8, a threaded connecting sleeve 64 having a frustoconical proximal opening 66 and internal threads 68 in a double-helical configuration is provided at the proximal end of the coil 58. The threaded connecting sleeve 64 is preferably provided with several internal distal ridges 70 which engage the barbs 62 during manufacture, and is also provided with a plurality of longitudinal external gripping ridges 72 and depressions 74 to facilitate twisting the threaded connecting sleeve 64 onto the threaded frustoconical tip 22 of the shaft 16.

A pull wire 80 is coupled at its distal end to the jaws 50, 52 and extends through the coil 58, the threaded connecting sleeve 64, the throughbore 24 of the shaft 16, and exits into the slot 18. A mating member 82 is provided at the proximal end of the pull wire 80. Referring to FIGS. 9 and 10, the mating member 82 generally has an elongate cylindrical distal portion 84, a frustoconical portion 85, a cylindrical central portion 86 having a relatively larger diameter, a cylindrical proximal grooved portion 88, and a conical proximal portion 90 preferably having a rounded apex 92. The elongate distal portion 84 has a bore 94 which receives the pull wire 80 so that the pull wire can be secured in the mating member by crimping. Preferably the distal portion 84 and the grooved portion 88 of the mating member have substantially the same outer diameter. The conical portion 90 tapers towards the apex 92 at an angle $\alpha$ relative to a longitudinal axis of the mating member, wherein the angle $\alpha$ is preferably approximately between 15°–25°. It is also preferable that the frustoconical portion 85 tapers towards the distal portion 84 at angle $\alpha$ relative to the longitudinal axis of the mating member. In order to facilitate insertion and removal of the mating member into the locking assembly, as described below, it is also preferable that the proximal rim 86a of the cylindrical portion 86 and the distal rim 90a of the conical portion be beveled.

Figure 11:
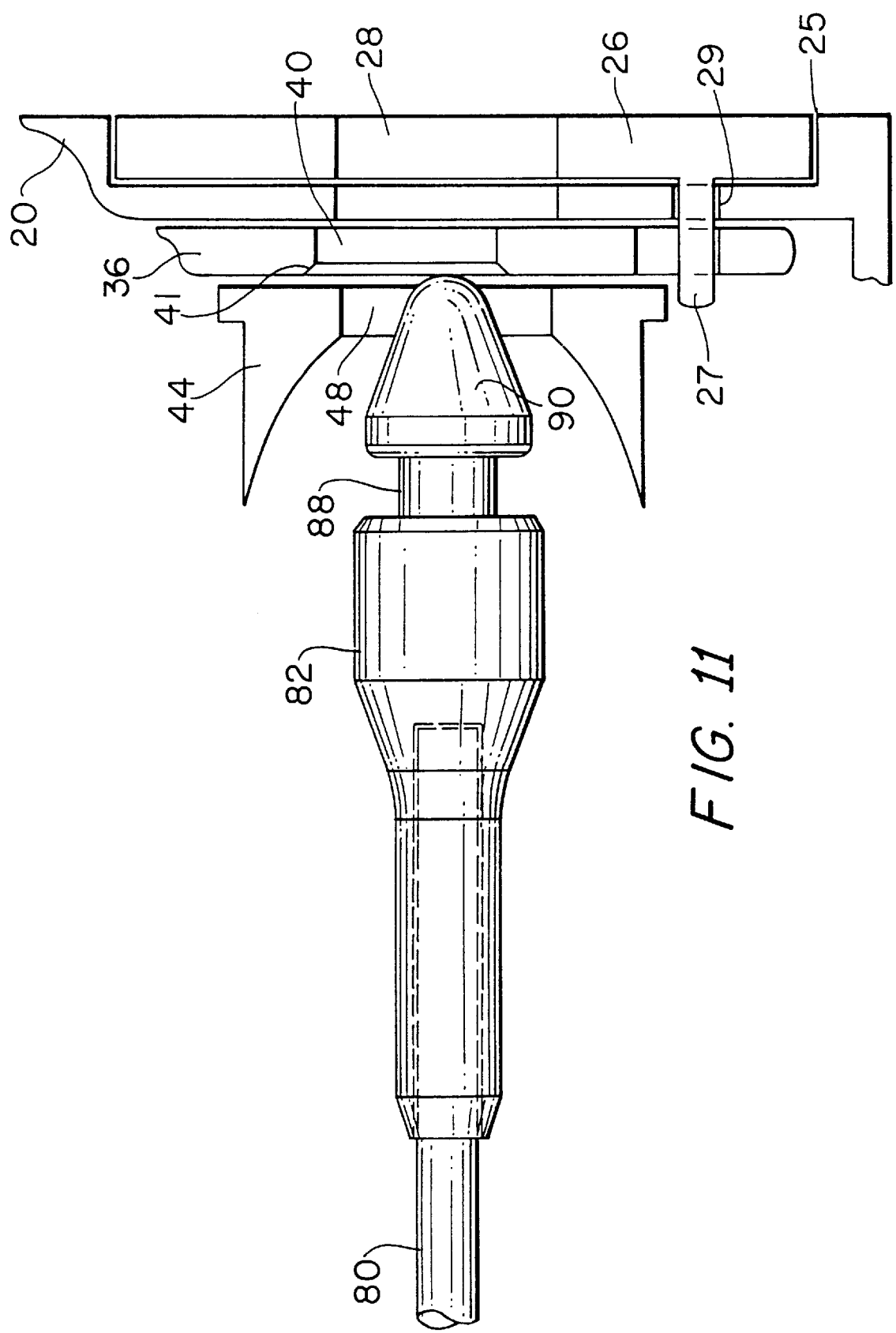
FIGS. 11–13 are broken side elevation views in partial section of various stages of engagement of the assembly of the grooved mating member with the locking assembly.
Figure 12:
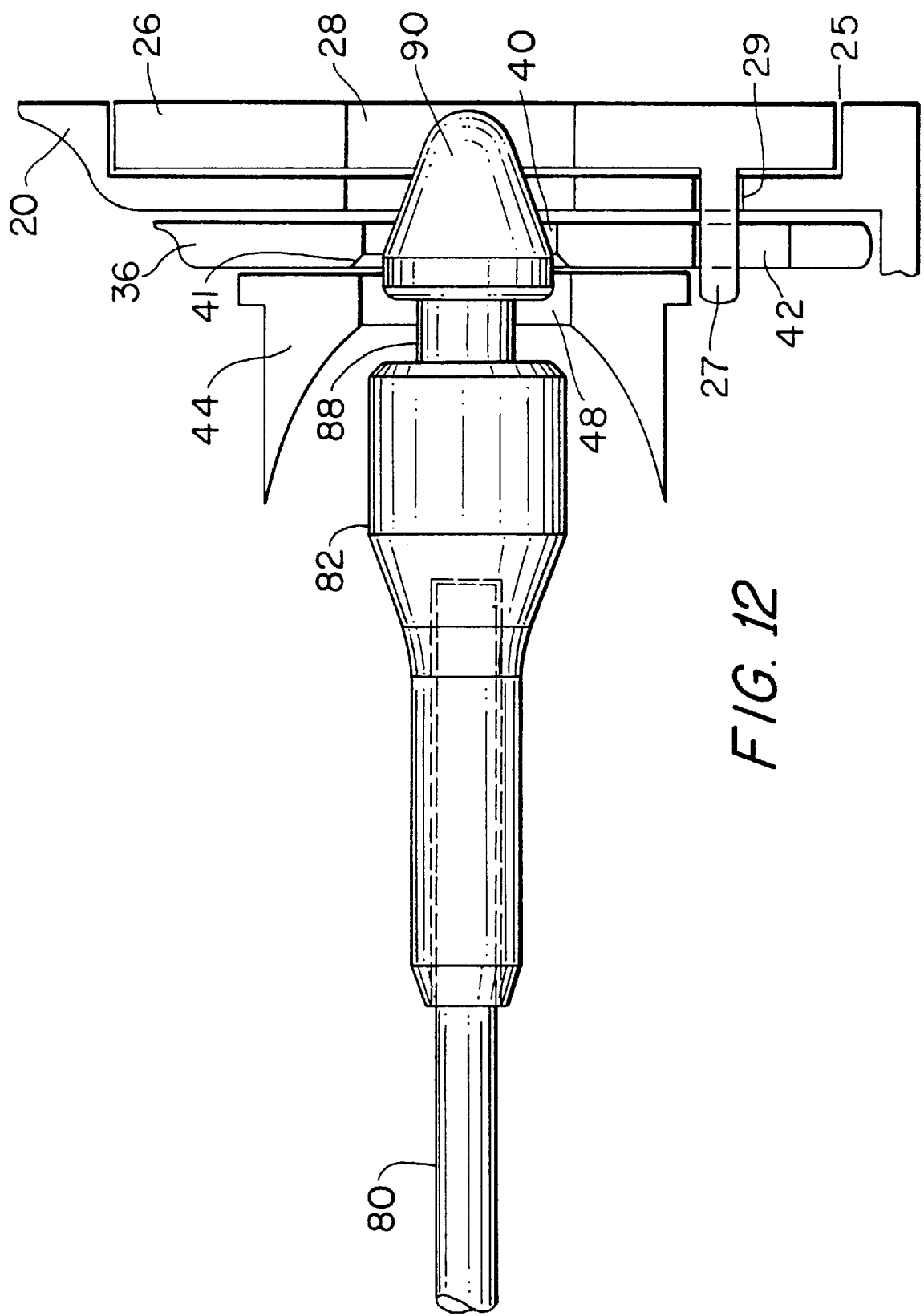
Figure 13:
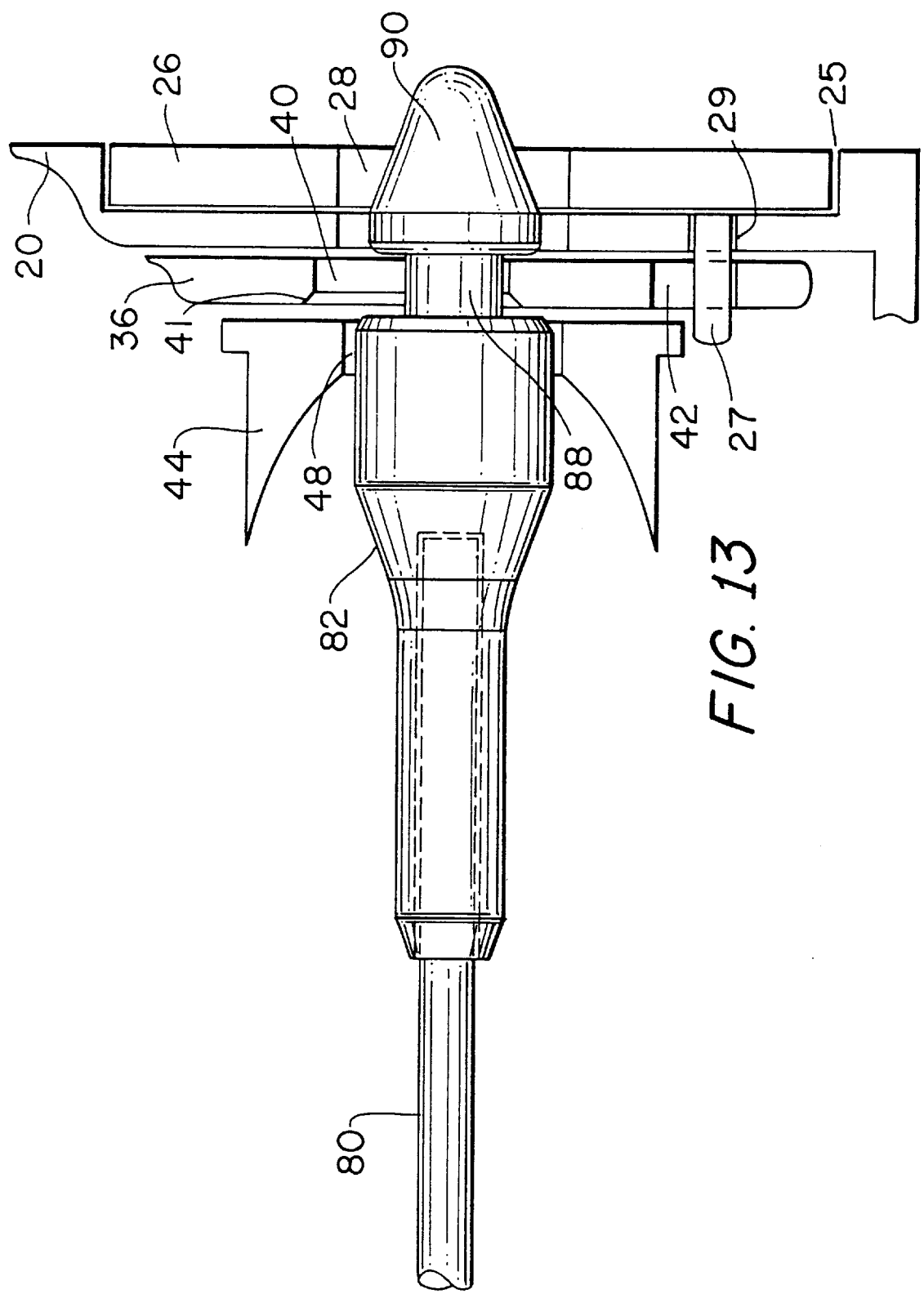

Turning to FIGS. 11 through 13, the latch 36 in the spool and the mating member 82 on the pull wire 80 are arranged such that the pull wire 80 is coupled to the spool 20 in a single motion. In particular, the mating member end of the pull wire 80 is inserted through the guide hole 48 so that the mating member 82 engages the latch 36 at the catch hole 40 (FIG. 11) and enters the catch hole and causes the latch to ride up the conical portion 90° of the mating member (FIG. 12). As the mating member is further inserted through the catch hole, the grooved portion 88 of the mating member intersects the latch, such that the latch engages the grooved portion and secures the mating member (FIG. 13).

After the pull wire 80 is coupled to the spool 20, the threaded connecting sleeve 46 at the proximal end of the coil 58 is easily connected to the shaft 16 by moving the threaded connecting sleeve onto the shaft tip 22 and applying a simple twisting motion. It will be appreciated that the frustoconical shapes of both the shaft tip 22 and the proximal opening 66 of the threaded connecting sleeve allow the threaded connecting sleeve to be substantially placed over the shaft tip prior to any twisting motion, thereby enabling a rapid coupling. The combination of the frustoconical shapes and the double helical threads permit a coupling of the coil 58 to the shaft 16 using only one half a turn of the connecting sleeve 46 relative to the shaft.

It will also be appreciated that the distal assembly can easily be removed from proximal handle. The connecting sleeve is first rotated relative to the shaft to release the coil from the shaft. The pull wire 80 is then uncoupled from the spool 20 by depressing the latch 36 until the latch releases the grooved portion 88 of the mating member 82. The mating member can then be pulled through the catch hole 40 and the guide hole 48 to release the pull wire from the spool. The proximal handle can then be reused with another distal assembly.

Turning to FIG. 14, a second embodiment of a biopsy forceps instrument, substantially similar to the biopsy forceps instrument of the first embodiment (with like parts indicated by numbers incremented by 100), is shown. A shaft 116 is provided having a frustoconical distal opening 195 and further having internal double-helical threads 196 and a throughbore 124. A threaded connecting sleeve 164 is provided at the proximal end of a shrink-wrap 160 covered coil 158. The threaded connecting sleeve 164 has a frustoconical proximal end 197 and external threads 198 in a double-helical configuration. The threaded connecting sleeve 164 is preferably provided with several internal ridges 170 for engaging barbs 162 of the shrink-wrapped coil, and is also preferably provided with a plurality of longitudinal gripping ridges 172 and depressions to facilitate gripping by the practitioner. The threaded connecting sleeve 164 can be connected to the shaft 116 by inserting the connector into the distal opening 195 of the shaft and by applying a simple twisting motion, such that the threaded connecting sleeve is rotated one half turn relative to the shaft. A pull wire 180 extends through the coil 158, the threaded connecting sleeve 164, the throughbore 124, and exits into the slot of the shaft where a mating member at the proximal end of the pull wire is engaged by a locking assembly provided in a spool on the shaft.

There have been described and illustrated herein embodiments of an endoscopic biopsy forceps instrument having a distal jaw assembly detachable from the proximal handle assembly. While particular embodiments of the invention have been described, it is not intended that the invention be limited thereto, as it is intended that the invention be as broad in scope as the art will allow and that the specification be read likewise. Thus, while a particular preferred shapes and angles have been disclosed for the mating member, it will be appreciated that other shapes and angles could also suffice. Furthermore, while the threaded connecting sleeve and shaft tip have been disclosed to have both frustoconical mating portions and double helical threads, it will be understood frustoconical mating portions and double helical threads can be used separately. Also, while crimping has been disclosed for coupling the pull wire to the mating member, it will be appreciated that soldering, welding, or gluing may also be used. Moreover, while the guide has been shown to have laterally and distally extending guide portions, it will be appreciated that the guide may also take the form of a rounded funnel. Furthermore, while the latch has been shown to be coupled to the cross block at the nub, it will be understood that other latch to cross block couplings can be similarly used. Moreover, while the end effectors have been shown to be forceps jaws, it will be appreciated that other end effectors may also be used, e.g., grippers, cutters, dissectors, and scissors. In addition, while one pull wire is disclosed to be connected to the distal jaws and to the mating member, it will be appreciated that two pull wires may also be used and similarly coupled. It will therefore be appreciated by those skilled in the art that yet other modifications could be made to the provided invention without deviating from its spirit and scope as so claimed.

We claim:

1. A biopsy forceps device, comprising:
   a hollow member having a proximal end and a distal end;
   an end effector assembly connected to the distal end of the hollow member;
   an actuator assembly for operating the end effector assembly, the actuator assembly including a coupling device and a first mating portion;
   a connecting member rotatable mounted on the proximal end of the hollow member and having a second mating portion for selectively engaging the first mating portion; and
   a control member slidably disposed within the hollow member, the control member having a distal end connected to the end effector assembly and a proximal end selectively engageable with the coupling device of the actuator assembly.

2. The device of claim 1, wherein the first mating portion is a first threaded portion and the second mating portion is a second threaded portion.

3. The device of claim 2, wherein the hollow member is flexible.

4. The device of claim 2, wherein the hollow member is a coil.

5. The device of claim 2, wherein the second threaded portion has external threads and the connecting member has internal threads.

6. The device of claim 5, wherein the threads of each of the second threaded portion and the connecting member has a frustoconical double helical configuration.

7. The device of claim 2, wherein the second threaded portion has internal threads and the connecting member has external threads.

8. The device of claim 7, wherein the threads of each of the second threaded portion and the connecting member has a frustoconical helical configuration.

9. The device of claim 2, wherein the control member is a pull wire.

10. The device of claim 1, wherein the connecting member has at least one external gripping ridge.

11. The device of claim 1, wherein the connecting member has at least one external depression.

12. A biopsy forceps device, comprising:
   a hollow member having a proximal end and a distal end, the proximal end having a threaded connecting member rotatably mounted thereon, the threaded connecting member including a first threaded portion, wherein the proximal end of the hollow member further includes at least one barb and the threaded connecting member has at least one ridge, wherein the ridge of the threaded connecting member engages the barb of the hollow member;
   an end effector assembly connected to the distal end of the hollow member;

an actuator assembly connected to the proximal end of the hollow member for operating the end effector assembly, the actuator assembly including a sliding member slidably mounted on a shaft, the sliding member having a coupling device, the shaft having a second threaded portion for engagement with the first threaded portion of the hollow member; and a control member slidably disposed within the hollow member, the control member having a distal end connected to the end effector assembly and a proximal end engageable with the coupling device of the sliding member.

13. A biopsy forceps device, comprising:

a hollow member having a proximal end and a distal end;

an end effector connected to the distal end of the hollow member;

an actuator for operating the end effector, the actuator selectively engageable with the proximal end of the hollow member and including a shaft;

a control member slidably disposed within the hollow member, the control member having a distal end connected to the end effector and a proximal end; and a sliding member slidably mounted on the shaft of the actuator, the sliding member including a spring-loaded coupling device configured to selectively engage the proximal end of the control member to selectively couple the control member to the sliding member.

14. The device of claim 13, wherein the spring-loaded coupling device includes a spring and a latch defining a catch hole configured to receive the proximal end of the control member, the spring biasing the latch such that an edge of the catch hole engages the proximal end of the control member.

15. The device of claim 14, wherein the proximal end of the control member includes a groove configured to engage the edge of the catch hole.

16. The device of claim 14, wherein the sliding member includes a guide hole adjacent the latch to guide the proximal end of the control member into the guide hole.

17. The device of claim 1, wherein the actuator assembly further includes a sliding member slidably mounted on a shaft and the sliding member includes the coupling device.

18. The device of claim 17, wherein the sliding member is a spool.

19. A distal biopsy forceps assembly for connection with an actuator, the actuator including a shaft having a first mating portion and a sliding member having a coupling device, the assembly comprising:

a hollow member having a proximal end and a distal end;

a connecting member rotatably mounted on the proximal end of the hollow member and having a second mating portion for selectively engaging the first mating portion;

an end effector assembly connected to the distal end of the hollow member; and a control member slidably disposed within the hollow member, the control member having a distal end connected to the end effector assembly and a proximal end engageable with the coupling device of the sliding member, wherein the distal biopsy forceps assembly may connect to the actuator by engagement of the second mating portion with the first mating portion and engagement of the proximal end of the control member with the coupling device of the sliding member.

20. The assembly of claim 19, wherein the first mating portion is a first threaded portion and the second mating portion is a second threaded portion.

21. The assembly of claim 20, wherein the hollow member is flexible.

22. The assembly of claim 20, wherein the hollow member is a coil.

23. The assembly of claim 20, wherein the connecting member has internal threads and the first threaded portion has external threads.

24. The assembly of claim 23, wherein the threads of the connecting member have a frustoconical double helical configuration.

25. The assembly of claim 20, wherein the connecting member has external threads and the first threaded portion has internal threads.

26. The assembly of claim 25 wherein the threads of the connecting member have a frustoconical helical configuration.

27. The assembly of claim 20, wherein the control member is a pull wire.

28. The assembly of claim 19, wherein the connecting member has at least one external gripping ridge.

29. The assembly of claim 19, wherein the connecting member has at least one external depression.

30. A distal biopsy forceps assembly for connection with an actuator, the actuator including a shaft having a first threaded portion and a sliding member having a coupling device, the assembly comprising:

a hollow member having a proximal end and a distal end, the proximal end rotatably mounting a connecting member having a second threaded portion engageable with the first threaded portion, wherein the proximal end of the hollow member further includes at least one barb and the threaded connecting member has at least one ridge, wherein the ridge of the threaded connecting member engages the barb of the hollow member;

an end effector assembly connected to the distal end of the hollow member; and a control member slidably disposed within the hollow member, the control member having a distal end connected to the end effector assembly and a proximal end engageable with the coupling device of the sliding member, wherein the distal biopsy forceps assembly may connect to the actuator by engagement of the second mating portion with the first mating portion and engagement of the proximal end of the control member with the coupling device of the sliding member.

* * * * *

UNITED STATES PATENT AND TRADEMARK OFFICE
CERTIFICATE OF CORRECTION

PATENT NO.: 6,007,560
DATED: December 28, 1999
INVENTOR(S): Gottlieb et al.

It is certified that an error appears in the above-identified patent and that said Letters Patent is hereby corrected as shown below:

Claim 1, col. 8, line 22, change "rotatable" to --rotatably--.

Signed and Sealed this

Twenty-fourth Day of October, 2000

*Attest:*

Q. TODD DICKINSON

*Attesting Officer*     *Director of Patents and Trademarks*